United States Patent [19]

Banko

[11] 3,996,935
[45] Dec. 14, 1976

[54] SURGICAL-TYPE METHOD FOR REMOVING MATERIAL

[75] Inventor: Anton Banko, Brooklyn, N.Y.

[73] Assignee: Surgical Design Corporation, New York, N.Y.

[22] Filed: Jan. 18, 1973

[21] Appl. No.: 324,814

Related U.S. Application Data

[62] Division of Ser. No. 799,476, Feb. 14, 1969, Pat. No. 3,732,858.

[52] U.S. Cl. .............................. 128/276; 128/305
[51] Int. Cl.² ................... A61B 17/32; A61M 1/00
[58] Field of Search ............. 128/276, 305; 3/1, 13
[56] References Cited

UNITED STATES PATENTS

| 1,532,455 | 4/1925 | Sunderland | 3/1 UX |
| 2,721,555 | 10/1955 | Jenney | 128/305 |
| 2,834,023 | 5/1958 | Lieb | 3/1 |
| 3,173,414 | 3/1965 | Guillant | 128/2 B |
| 3,526,219 | 9/1970 | Balamuth | 128/305 |
| 3,538,425 | 9/1970 | Banko | 128/305 |
| 3,553,299 | 1/1971 | Thiele | 3/13 X |
| 3,565,062 | 2/1971 | Kuris | 128/305 X |
| 3,589,363 | 6/1971 | Banko | 128/276 |
| 3,614,953 | 10/1971 | Moss | 128/305 |

Primary Examiner—Channing L. Pace
Attorney, Agent, or Firm—Darby & Darby

[57] ABSTRACT

The invention deals with surgical methods for the removal of tissue and other objects from the body of humans or animals, for example, foreign objects from the eye, including blood clots and the lens of the eye, by inserting a pair of jaws for engaging the object and removing portions thereof as required by movement of the jaws relative to each other.

22 Claims, 22 Drawing Figures

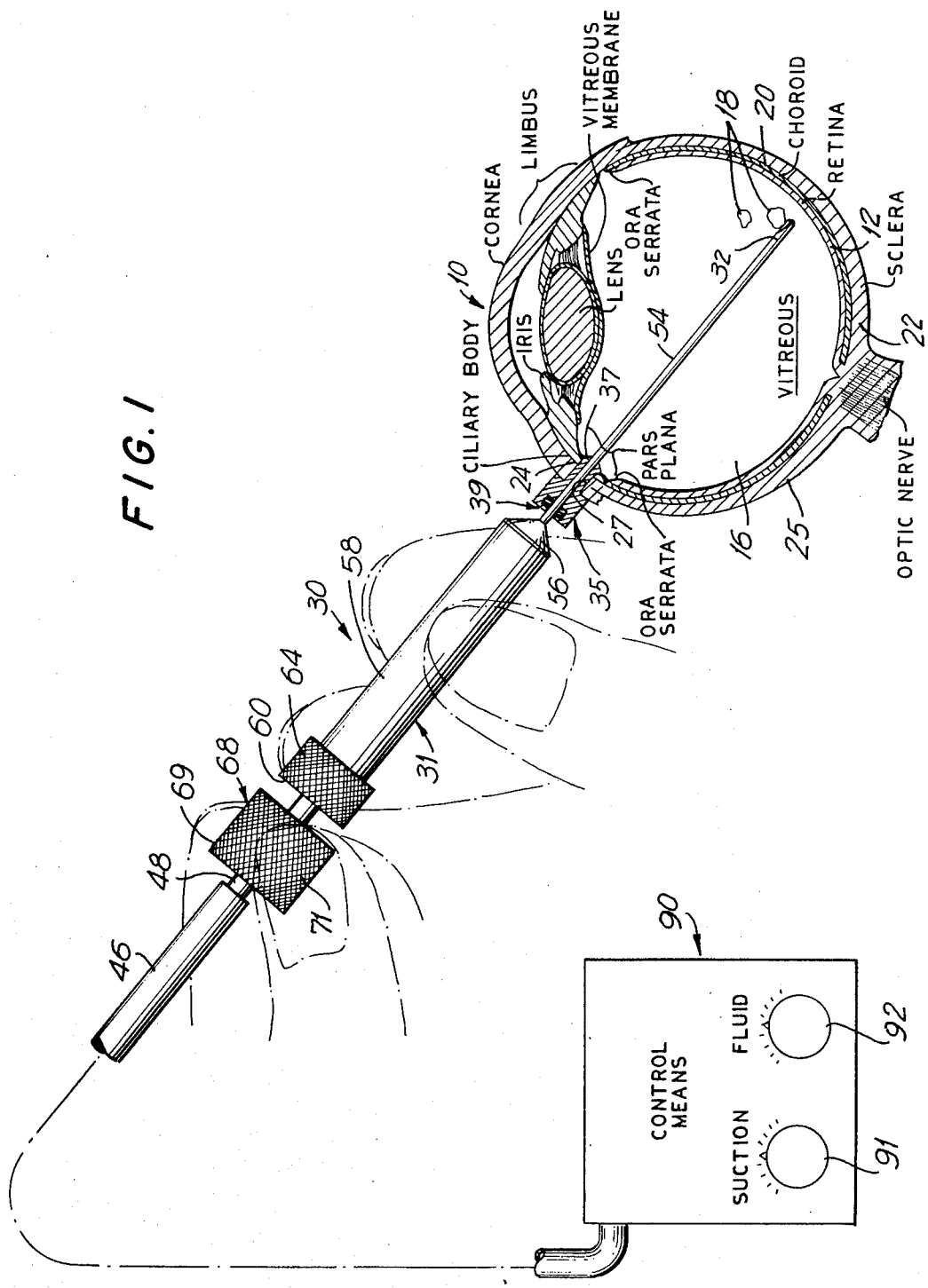

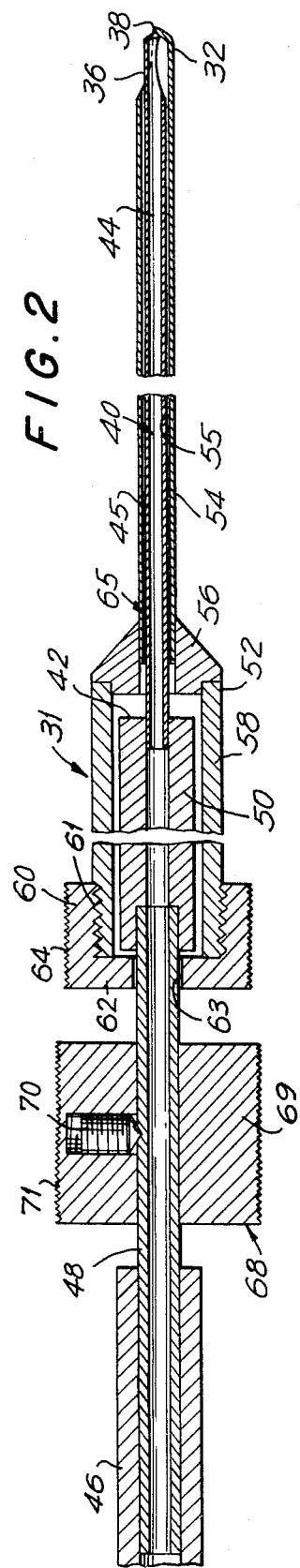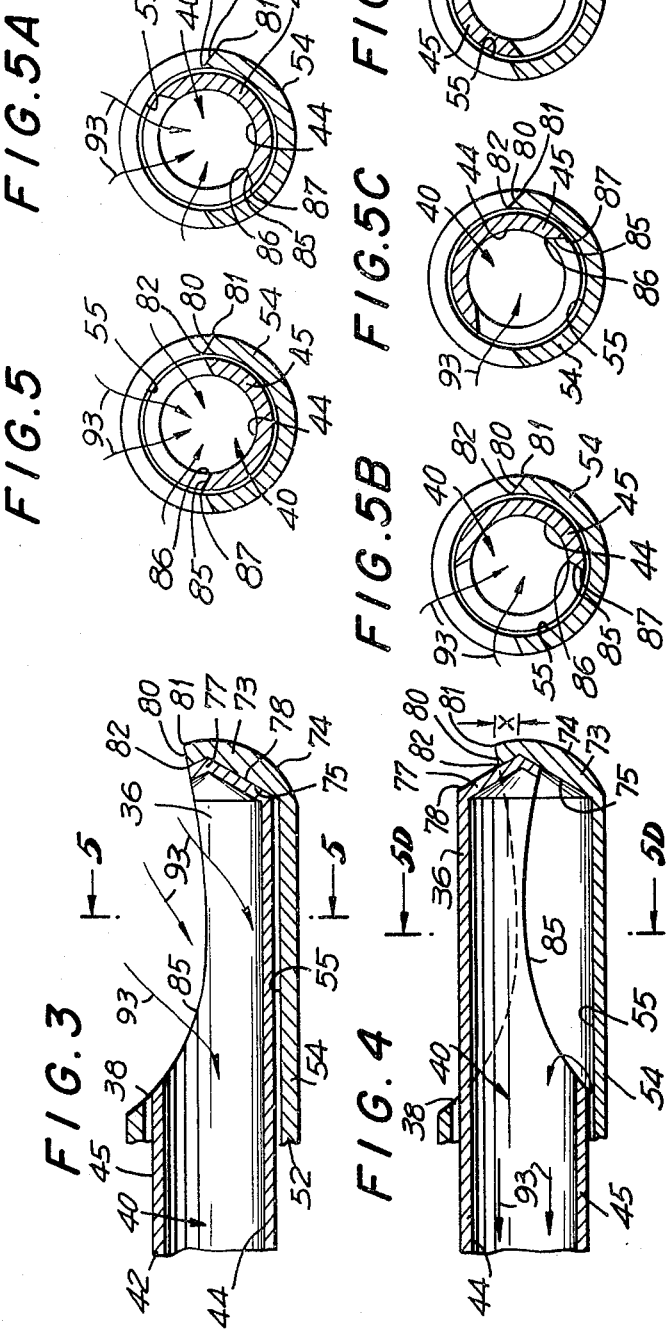

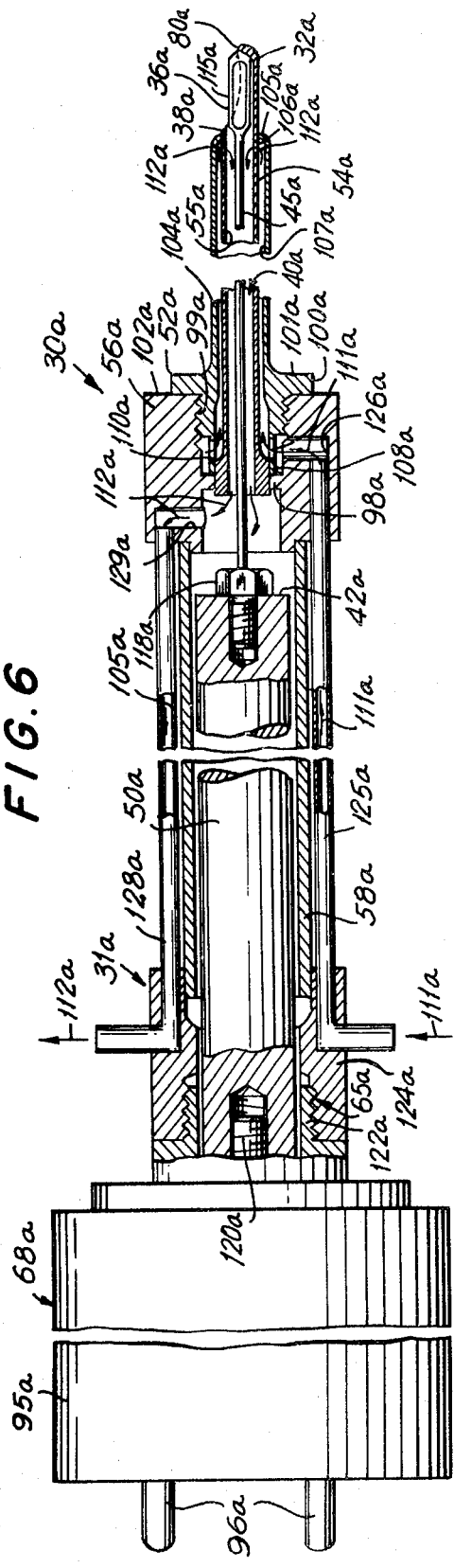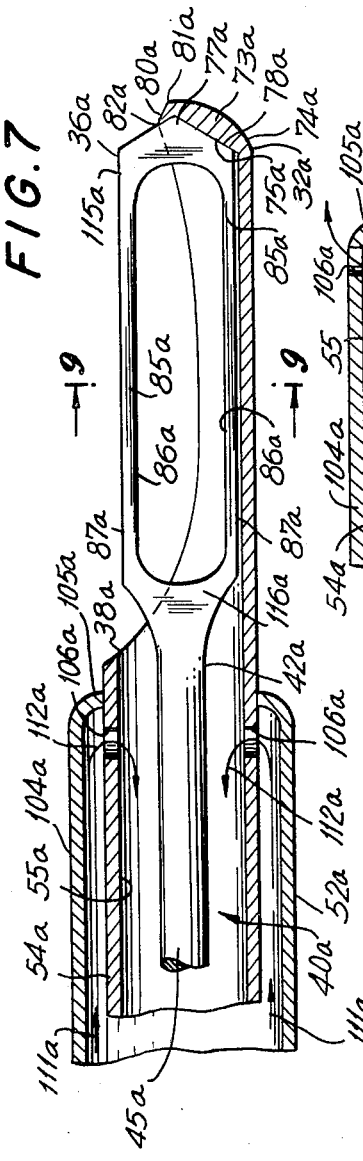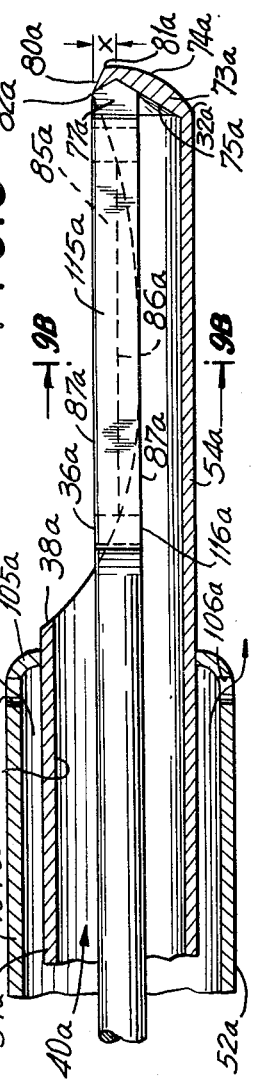

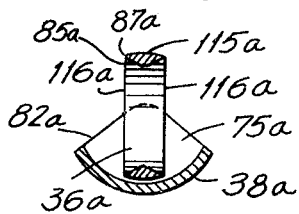
FIG. 9
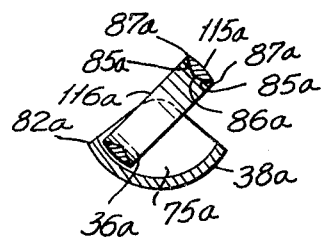
FIG. 9A
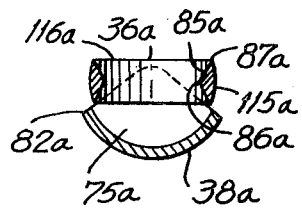
FIG. 9B
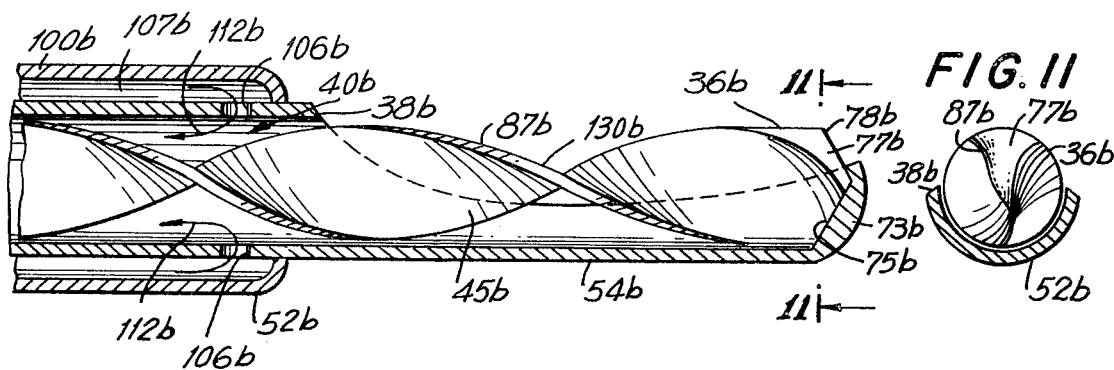
FIG. 10
FIG. 11
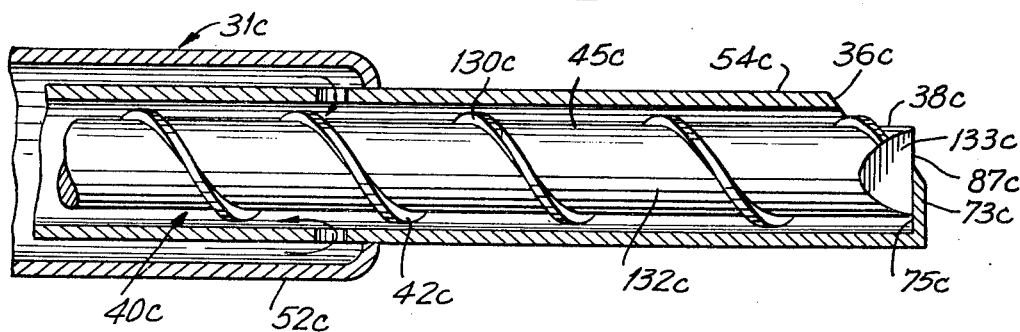
FIG. 12

SURGICAL-TYPE METHOD FOR REMOVING MATERIAL

This is a division of application Ser. No. 799,476, filed Feb. 14, 1969 now U.S. Pat. No. 3,732,858.

CROSS-REFERENCE TO RELATED APPLICATION

This application is a division of copending application Ser. No. 799,476, filed Feb. 14, 1969, now U.S. Pat. No. 3,732,858, issued May 15, 1973 which application in turn is a continuation in part of applicant's then co-pending application Ser. No. 762,286 filed on Sept. 16, 1968, now U.S. Pat. No. 3,528,425, issued Sept. 15, 1970.

BACKGROUND OF THE INVENTION

The present invention relates generally to improvements in surgical procedures related to the eye, and more particularly to methods and apparatus for the removal of blood clots and other impurities, including the lens from the eye.

The outstanding and unexpected results obtained by the practice of the method and apparatus of the present invention, are attained by a series of features, steps and elements, working together in inter-related combination, and may be applied to biological organisms in general and particularly the eyes of humans, and hence will be so illustrated and described. The present invention may be used to perform a biopsy at any portion of the anatomy as well.

Applicant has found that in order to perform various exploratory, diagnostic, or other surgical procedures with respect to the eye, that it is neccessary for an incision or opening to be formed through the wall thereof such that the instrumentation necessary might be inserted therethrough. When the procedure intended is completed it then becomes necessary to close the opening and permit the incision in the wall of the eye to properly heal such that the eye might function in a proper manner. In applicant's co-pending patent application referred to above, the process of forming and closing the opening is disclosed, and which incision might be formed for use in accordance with the present invention. To facilitate the discussion of applicant's present invention dealing with the removal of blood clots or the lens of the eye, reference is made to the co-pending application to merely illustrate one form of initial surgical procedure that might be conducted to gain access to the interior of the eye for practising the present invention.

By way of illustration and not limitation, once an incision has been made and a passageway formed from the exterior to the interior of the eye then a variety of instruments may be inserted within the passageway to accomplish physical tasks. In accordance with the present invention the instrumentation is designed to be inserted through the passageway for removing any object or deposit, such as blood clots, tissue and impurities from vitreous material contained within the eye as well as the removal of part or all of the vitreous or the lens from the eye and its replacement with another material.

The term "object" or "deposit" as used herein is intended to include any portion of the body that is to be removed partially or entirely therefrom for whatever purpose it is so desired. By way of example and not limitation, this may include a blood clot, a growth, such as a tumor, or other impurity in the eye, or any other portion of the body however formed, the lens of the eye, healthy, diseased or dead tissue for a biopsy or other reason.

REMOVAL OF BLOOD CLOTS

Before proceeding to the details of the invention, let us first review briefly generally known facts of the eye and the formation of deposits or objects of which removal thereof is desired. The retina of the eye is attached to the underlying choroid at the optic nerve border posteriorly and at the ora serrata anteriorly. Between these two points it is in contact with but not attached to the choroid. The retina covers the entire inner aspect of the eyeball posterior to the era serrata. The era serrata is the junction of the retina and the ciliary body, in the average eye it is about 8mm posterior to the limbus. The retina is composed of inelastic nerve tissue, consisting of ten distinct different layers, normally it is transparent, when detached it appears gray. Contained within the eye in front of the retina is the vitreous material in which deposits are formed which may include blood clots, other impurities, as well as tissue both healthy or diseased.

Blood clots due to traumatic ruptures of retinal vessels or other causes like diabetes, mellitue, hypertension, peri vasculitis or retinal detachment are often disturbing to the vision. Hemorrhage into the vitreous is an uncommon but serious disorder. There may be sudden and complete loss of vision in the affected eye. The blood often remains in the vitreous for months or forever.

The retina is usually damaged by prolonged intimate contact with blood elements. If the vitreous clears it is possible that the retina is detached and vision may be restored by surgical reattachment. Beside blood clots there may be other impurities in the vitreous or aqueous humor. The humor as a whole can also be spoiled.

At the present time there is no effective, reliable or safe means for removal of such blood clot deposit known to the applicant. In certain parts of the eye a single small blood clot can not be practically removed from the eye. The exchange of the vitreous as a whole, to applicant's knowledge was never performed routinely. The vitreous is a thick transparent gelatinous body which encompasses two-thirds of the volume and weight of the eye. Because of the high viscosity the vitreous cannot be aspirated through a hypodermic needle with a syringe.

REMOVAL OF LENSES

A cataract is an epacity of the lens of the eye requiring cryosurical techniques to obtain removal of the lens. The cryoextraction usually requires lens extraction. At the present time, only a congenital, up to the age of twenty, cataract can be aspirated through a relatively small incision. Aspiration is possible because of the semi-fluidic consistency of the lens.

However when the lens material (cortex and nucleus) is hard and cannot be aspirated routinely, a 20mm incision is made at about 3mm from the limbus, the incision runs for 180° from 9 o'clock to 3 o'clock. There are two principal types of lens extractions intracapsular and extracapsular (just removing lens leaving capsule).

The intracapsular extraction consists in removing the lens within its capsule, lens and capsule is grasped and pulled gently from the eye. This operation has become the standard cataract procedure.

The extracapsular operation requires a rupture of the anterior portion of the capsule first, the lens cortex and nucleus are removed from the eye leaving the posterior capsule behind, this kind of operation is indicated in some congenital and traumatic cataract. Up to the age of twenty the lens is attached to the vitreous and intracapsular extraction will surely lead to considerable loss of vitreous and possible destruction of the eye.

Prior to the extraction of the lens an enzyme is used, which has a proteinoceous substance that accelerates reaction at body temperature. It has a specifically tie effect on the zonules (tougher at ages 20–50) and so making the removal of the lens much easier. The lens is usually grabbed by a special lens capsule forcept or cyro probe and pulled from the eye. Sutures are now ties and the anterior chamber is reformed if necessary by injection of saline. Occasionally, the cataract operation is combined with corneal transplant, the lens and capsule is removed through the front trepline opening of about 8mm diameter. In each instance the pupil has to be widely dialated.

OBJECTS OF THE INVENTION

An object of the present invention is to provide an improved method and apparatus for performing surgical procedures with respect to the eye and other portions of the anatomy.

Another object of the present invention is to provide an improved method and apparatus for removing objects from within the eye.

Another object of the present invention is to provide an improved method and apparatus for the removal of blood clots from the eye in a safe manner.

Another object of the present invention is to provide an improved method and apparatus for opening the eye and introducing instrumentation therein and removing the lens of the eye.

Another object of the present invention is to perform a cataract operation in which the lens is removed and replaced with a fluid.

Other objects and advantages of this invention will become apparent as the disclosure proceeds.

SUMMARY OF THE INVENTION

The present invention is directed to the removal of objects from humans and animals in vive by surgical procedures and particularly those in the eye, as by first forming an opening to gain access to the interior thereof and inserting therein removal means having a pair of jaws movable relative to each other at substantially one end of the removal means. Passage means are provided in the removal means in communicating relationship to the jaws and vented to the atmosphere to provide an exit of the removed material therefrom. The jaws are positioned proximate to the object for engagement therewith, which engagement is maintained by providing a differential pressure at the removal site, either by a venting of the passage means to the atmosphere, since the pressure within the eye is generally greater than the atmosphere it will force the object against the jaws and if a viscous material will effectuate a flow thereof into the passage means. On the other hand if the object is of a hardened substance then a suction force may be applied through the passage means to obtain the intimate contact therebetween. Accordingly, the suction force may be used even on viscous objects to increase the movement thereof.

Once the object is in place and pressural contact is maintained, relative movement of the jaws is obtained by drive means so as to sever any material of the object extending therebetween as the jaws are moved relative to each other, with the removed material then contained in the passage means. A suction force may be applied to the passage means to remove the material therefrom.

In accordance with one aspect of the invention the jaws are adapted to be moved from an open position permitting material to enter the passage means, to a closed position substantially preventing material from entering the passage means.

In accordance with another aspect of the invention the jaws may define cutting edges such as for use in the extraction of the lens and/or the capsule through a small (2mm) incision at the limbus after the pupil is dilated. The incision may be made with a specially designed two edge cutter, which produces the same approximate incision every time. Part of the anterior capsule may be removed so that the cutting edge can start chopping the softer cortex and later the nucleus and the remainder of the capsule or the cutting tip of the instrumentation may be pressed against the anterior capsule to cut off part of its first. The instrumentation then continues to cut away the lens and the material is removed, which lens may be replenished with a fluid as a substitute thereof, all in accordance with the invention.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1, is a somewhat schematic view of a human eye having the instrumentation inserted therein for removal of a foreign object therefrom, in accordance with the present invention;

FIG. 2, is a side view in section of the instrumentation of the present invention;

FIG. 3, is an enlarged fragmentary side view in section of the jaws in their open position;

FIG. 4, is an enlarged fragmentary side view in section of the jaws in their closed position;

FIG. 5, is a sectional view along the line 5—5 of FIG. 3;

FIGS. 5A, 5B and 5C, are sectional views similar to FIG. 5, illustrating the progressive movement of the jaws from their open to closed position;

FIG. 5D, is a section view along the line 5D—5D of FIG. 4 and illustrating the jaws in their closed position;

FIG. 6, is a side view substantially in section illustrating another form of instrumentation in accordance with the present invention;

FIG. 7 is an enlarged fragmentary side view in section of the jaws illustrated in FIG. 6;

FIG. 8, is an enlarged fragmentary side view in section of the jaws illustrated in FIG. 6 in another position;

FIG. 9, is a sectional view along the line 9—9 of FIG. 7;

FIG. 9A, is a sectional view similar to FIG. 9, showing the jaws in a different angular position with respect to each other;

FIG. 9B, is a sectional view along the line 9B–9B of FIG. 8, showing the jaws in another angular position relative to each other;

FIG. 10, is an enlarged fragmentary side view in section of another form of jaws in accordance with the present invention;

FIG. 11, is a sectional view along the line 11–11 of FIG. 10;

FIG. 12, is an enlarged fragmentary side view in section of another form of jaws in accordance with the present invention;

PREFERRED EMBODIMENTS OF THE INVENTION

Figure 13:
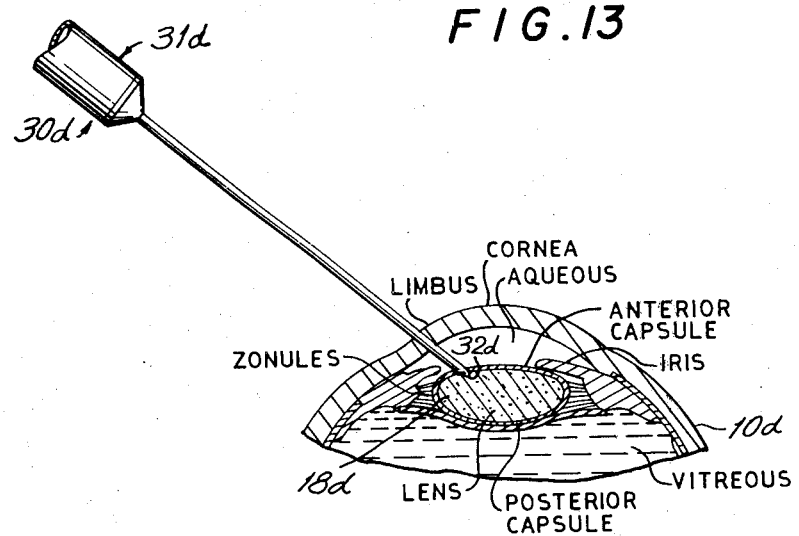
FIG. 13, is a somewhat schematic view of a human eye having the instrumentation inserted therein for removal of the lens thereof.
Figure 14:
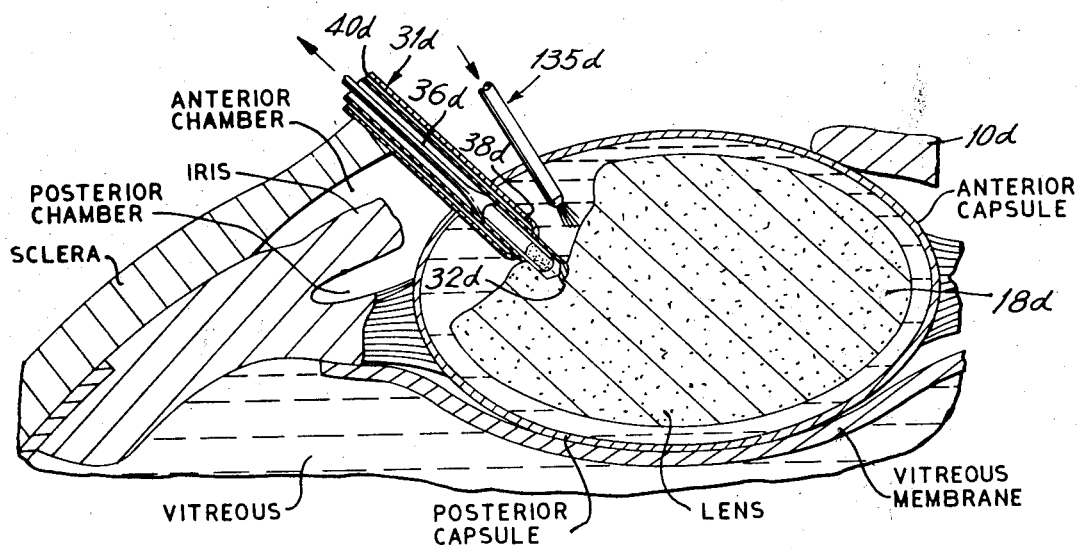
FIG. 14, is an enlarged sectional view illustrating the removal procedure for the eye lens.

Referring now to the drawings and particularly to FIG. 1 thereof, we see the schematic representation of an eye 10 having the various portions thereof including a retina 12, choroid 20 and sclera 22. The vitreous body or material 16 is contained within the retina 12 and vitreous membrane and is seen to include foreign objects 18 which say be in the form of blood clots or other impurities that are desired to be removed from within the eye 10. The wall 25 is intended to define any portion of the eye which when pierced will connect the interior of the eye to the exterior and will generally include all, or portions, of the retina 12, cheroid 20 and sclera 22, or the sclera 22 and ciliary body 24.

Once the blood clot 18 is detected then the surgical procedure is initiated, which first includes, in accordance with the teachings of applicant's copending patent application, the forming of an incision or opening 27 in the eye 10, to permit the insertion of instrumentation 30 in the form of a probe therethrough to reach the specific area to be treated. The removal process of the foreign object as hereinafter described in greater detail, is capable of being used not only for the eye but for various other operative procedures and uses hereinabove disclosed, both with the eye and other portions of the anatomy and is accordingly so described and intended.

Once the opening 27 is formed the instrumentation 30 is inserted therein such that the removal means 31 has its tip or distal end 32 thereof, positioned within the vitreous material 16 contained in the eye 10 to obtain a continuous severing and removal of the blood clot 18 therefrom.

The supporting means 35, which may be of a metallic or thermoplastic material, as seen with respect to FIG. 1, extends through the wall 25 and is positioned in and tightened in the incision or opening 27 by a double mattress suture not shown. The supporting means 35 should have the ability to rotate within the opening 27. To provide a seal with the removal means 31 and facilitate its sliding, the supporting means 35 should have a minimum outside diameter to be inserted into the incision 27, and possibly supported and rotated by a micromanipulator. Finally the supporting means 35 should eventually provide for an increase in volume of the vitreous cavity in order to reduce the pressure in the eye 10, during the operation. The supporting means 35 comprises a tubular body portion 37 which may be of circular cross-sectional area so that it may be rotatable after it is seated through the wall 25 of the eye 10 and includes an opening connecting the interior of the eye to the exterior, and extending from the front end to the rear end thereof. Sealing means 39 is provided in the opening to prevent any of the internal fluids of the eye from flowing out when the instrument 30 extends therethrough. The sealing means 39 may include a sealing member 68, which may be in the form of an o-ring to provide the sealing engagement with any element inserted within the opening. Due to the viscosity of the vitreous material a close tolerance at one point in the opening between the removal means and supporting means may be sufficient to provide the sealing engagement.

FIGS. 1 through 5D illustrate one embodiment of the present invention in which the instrumentation 30 is illustrated in one form thereof, in which the removal means 31 is inserted within the eye 10 and is retained in position by the supporting means 35 extending through the opening 27 in the wall 25, in accordance with applicant's copending invention. Once the supporting means 35 is placed in position the removal means 31 is inserted through an opening extending therethrough and the exact position is obtained by the surgeon such that the distal end 32 thereof is placed proximate to the object 18 for engagement with the jaws 36 and 38, sometimes referred to as the inner jaw and outer jaw respectively for convenience, of the removal means 31. The removal means 31 is seen to include passage means 40 such that when the material is removed from the object 18 by the pair of jaws 36 and 38, which are in communicating relationship to the passage means 40 at proximately one end thereof, the material may be conveniently removed from the removal means 31 which is adapted to be inserted in the body of a human being or other animal in vive.

The removal means 31 includes an elongate inner assembly 42 with a central longitudinal flow passage 44, which in this embodiment forms the passage means 40, and extends through an elongated tubular inner jaw member 45 having the jaw or port 36 at its terminal end, and at its opposite end we have the inner assembly 42 adapted to be releasably connected with the lower end of a fluid conducting tube member 46 which is in communicating relationship with the flow passage 44 by means of supply member 48 which is tubular and is interfitted within the conducting member 46 at one end thereof and having a tubular extension member 50 between the jaw member 45 and supply member 48, all of which are in interfitting relationship to each other such that the material removed from the object 18 may be moved by various means through the passage means 40 and eventually removed from the removal means 31.

The removal means 31 further includes an elongate, outer assembly 52 rotatably engaged about and extending below the inner assembly 42 and includes an inner tubular jaw member 54 with a passageway 55 extending therethrough and having the jaw or port 38 at its terminal end and at its opposite end connected to a support member 56 which in turn is connected to a tubular coupling member 58 having a gripping member 60 secured thereto as by threads 61 with an annular wall portion 62 having an opening 63 through which the supply member 48 extends. To facilitate the angular movement between the jaws a gripping surface 64 which may be in the form of knurling is provided on the exterior or the gripping member 60.

The gripping member 60 as seen in FIG. 1, may be in part engaged by a finger of the user such that one assembly may be controlled and moved angularly relative to the other since the inner assembly 42 and outer assembly 52 includes mounting means 65 for supporting the respective inner and outer assemblies for relative angular displacement relative to each other. The mounting means 65 may include axially spaced apart support members or bushings for higher rotatably mounted members, or as in the present embodiment it has been found that a minimal spacing between the respective outer diameter of the inner jaw member 45 and the passageway 55 of the outer jaw member 54 is sufficient to permit hand movement therebetween. The drawings are shown with a slight spacing therebetween for convenience in illustration.

To effectuate relative movement drive means 68 is provided such as by a cellar 69 secured as by mounting screw 70 to the supply member 48 and which collar 69 may have an outer textured surface 71 such as by knurling such that it may be manually controlled to facilitate its movement. As seen in FIG. 1, the fingers of the user grasp the gripping member 60 and collar 69 and move same relative to each other in an angular plane to obtain revolvement of the jaws 36 and 38 relative to each other.

As seen particularly in FIG. 2, the respective inner and outer assemblies 42 and 52 are in coaxial alignment with each other and mounting means 65 is provided to keep them relatively spaced for the respective angular rotation or displacement of the jaws 36 and 38 relative to each other for material removal as hereafter described. The outer assembly 52 and inner assembly 48 are shiftable into and out of register with the respective jaws 36 and 38 upon relative rotation of the inner and outer assemblies relative to each other such that the amount of material that is removed may be controlled. The mounting means 65 due to the relative slow rotation or angular displacement of the configuration shown in FIG. 2, which is manually operated might be anywhere from a fraction of a revolution to several thousand revolutions per minute, although the respective jaw configuration may be used with a power driven device as hereafter described, such that the dimensional relationships of the inner jaw member 36 to the outer jaw member 38 is sufficient to act as the mounting means 65 such that a sliding fit is obtained to permit the angular rotation therebetween.

The related angular movement between the respective inner jaw member 45 and outer jaw member 54 is illustrated in FIGS. 3-5D, and as hereafter discussed this embodiment of the invention utilizes the principle that the respective jaws 36 and 38 are formed such that they may be moved relative to each other from an open position as seen in FIGS. 3 and 5 to a closed position as see in FIGS. 4 and 5D, with the angular changing from the open to closed position illustrated in FIGS. 5A, 5B and 5C.

It is appreciated that the actual pressure within the vitreous material 16 is greater than that of the atmosphere and accordingly we have a differential pressure established between the atmosphere and the inner portion of the eye 10. This differential pressure in accordance with the present invention may also be established by applying an exterior force to any portion of the wall 25 of the eye or by applying a suction force through the removal means 31 and through the passage means 40 such as to facilitate the flow of the removed material within the passage means 40 and thereafter from within the removal means 31. The jaws 36 and 38 are shiftable into and out of register with each other such that in practicing the invention we initially insert the instrumentation 30 through an opening formed in the supporting means 35 while the jaws are in their closed position as seen in FIGS. 1 and 2, and maneuver same until the distal end 32 thereof is as seen in FIG. 1 in proximity to the object 18 which is to be partially or entirely removed therefrom. The particular consistency of the object 18 will generally indicate whether the respective jaws 36 and 38 define cutting edges, and this will be dependent upon the viscosity of the object which is being encountered.

The jaws 36 and 38, may be formed to define cutting edges for severing or cutting of portions of the object 18 extending therebetween, and as illustrated the outer jaw member 54 has a front end portion 73 having a contoured exterior surface 74 to facilitate its movement through the viscous material 16 and an inner seat 75, shown as a conical depression for receiving the complimentary shaped front end portions 77 of the inner jaw member 45 with its conical exterior surface 78 which mates with the seat 75 for coaxial alignment therewith.

The outer jaw member 54 has therein the outer jaw defining opening or port 38 which is in communicating relationship to the flow passageway 55 and defines an elongated or oval shaped surface 80 having an outer edge 81, and inner edge 82 preferably sharp to define a cutting edge with the surface 80 inclined upwardly towards the cutting edge 82 from the outer edge 81. The forward extremity of the outer edge 81 or surface 80 should be above the axis of the outer jaw member 54, and preferably a distance represented by the dimension X which is at least equal to the wall thickness of the outer jaw member 54, so as to prevent rotation of tissue or other substances pulled by the penetrating point or cutting edges.

The inner jaw member 45 is similarly formed with the inner jaw defining an opening or port 36 which is in communicating relationship to the flow passage 44 and defines an elongated or oval shaped surface 85 having an inner edge 86 with a spaced apart outer edge 87 preferably sharp to define a cutting edge with the surface 85 tapering upwardly from inner edge 86 to the outer edge 87.

To obtain the removal of the object 18 as contained in the passage means 40 control means 90 is utilized and is connected to the removal means 31 by the conducting member 46. To obtain a differential pressure at the removal site or passage means a suction force may be applied through the conducting member 46 which is in communicating relationship to the passage means 40 and the amount of force may be controlled by knob 91 such that the removed material is sucked into the control or other means and disposed of. A fluid supply control knob 92 is illustrated for use with the embodiment of the invention in which a fluid supply is provided to form a suspension with the removed material to facilitate its removal. If fluid is desired in accordance with the embodiment illustrated in FIGS. 1-5D it may intermittently be supplied through the passage means 40 when the suction is not being applied.

OPERATION OF APPARATUS IN FIGS. 1-5D

The instrumentation 30 is adaptable to be used for removing objects 18 having various hardness characteristics, which if viscous, by flowing between the jaws 36 and 38 and then separating the mass of the object 18 from itself or the environ it is in, or by actually cutting slices thereof for hardened substances.

In accordance with one aspect as illustrated in FIG. 1, the object 18 may be of a viscous material, or having a viscosity which is capable due to the differential pressure either existing or to be established to obtain a flow thereof into the passage means 40. Assuming this to be the case for viscous materials, the removal means 31 is positioned proximately to the object 18 and the jaws 36 and 38 are then moved initially to their open position as seen in FIGS. 3 and 5 by angular rotation of the drive means 68 as illustrated in FIG. 1, from their closed to open position, this occurring after positioning the removal means 31 proximate to the object for engagement with the jaws 36 and 38. Either before or upon the jaws reaching their open position we have due either to the greater pressure within the eye 10, than in the passage means 40 which is in communicating relationship with the atmosphere, a differential pressure on the object 18 which is sufficient to obtain a flow thereof within the passage means 40 when the jaws are in their open position such that there is a partial if not entire movement of the object into the passage means 40. Once all the material of the object 18 is in the passage means 40 or the movement of the material has stopped (due to insufficient differential pressure or increased resistance to motion) then we are affecting relative movement of the jaws 36 and 38 from their open position to closed position, progressively as seen in FIGS. 5A, 5B and 5C, a severing or cutting off of all or part of the material of the object 18 extending between the jaws 36 and 38 as they are moved relative to each other resulting in all or a portion of the object remaining within the passage means 40 when the jaws are in their closed position as seen in FIGS. 4 and 5D. At this instance the entire instrumentation might be removed if the amount of material contained in the passage means 40 is adequate, or the cycle of revolving the jaws from the open to closed position may be repeated as often as required, the entrapped material by adjusting the suction knob 91 may remove the material from the passage means 40.

The maintaiing of a differential pressure between the passage means 40 and essentially the envion of the object 18 is done to retain them in substantially fixed position to each other during the relative movement of the jaws 36 and 38. The force may be transmitted to the sight of removal in the direction of arrow 93 by proper coupling of the conducting member 46 to the control means 90 which is shown to include the knob 91 for controlling suction and another knob 92 for controlling fluid. The fluid control knob 92 is illustrated as being a part of the control means 90 although it is not contemplated for use necessarily with the embodiment illustrated in FIGS. 1-5D but as hereafter explained is used with other embodiments of the invention.

The suction means which gives us the suction force is selected depending upon the viscosity and type of material from which the object is made so that we are assured of the positioning of the object 18 in abutting relationship to the distal end 32 of the removal means 31. The suction force may be used with a viscous object in that by applying same the removed material continues to be removed out from within the passage means 40 into the control means 90 so that the object contained within the passage means 40 is continuously moved therealong and does not clog or block the jaws in their open position.

When the object 18 is of a hardened material or substance such that a flow thereof is not anticipated, or the rate of flow is not sufficient, then it is desired that sharp edges which act as cutting edges 82 and 87 of the outer jaw 38 and inner jaw 36 respectively be provided so as to obtain by continued rotation of the inner and outer assemblies 42 and 52 respectively by the drive means 68, a progressively contacting, cutting and removal of material of the object 18 as the jaws are repetitively closed. In this instance the inherent differential pressure may be such as to obtain a positionment of the object 18 abutting one or both of the jaws 36 and 38 but as the cutting continues it is preferable that a suction force be relied on to retain the object 18 and removal means 31 in fixed position to each other. Thus, if the object illustrated in FIG. 1, is of a hard material and essentially the removal means 31 is positioned in its closed position adjacent the object 18 and as discussed before the cutting edges 82 and 87 are in communicating relationship with the passage means 40 at proximately one end thereof, are then moved from their initially closed position to an open position to begin the removal process. By applying an ample suction force through the passage means 40 to the object 18 it is retained in continuous contact with one of the jaws 36 and 38 and by affecting relative movement of the cutting edges 82 and 87 from their open to closed position they can progressively contact, cut and thereby remove a layer of material from the object 18. The configuration of the jaws as well as the cutting edges as to both size and configuration will vary with respect to the size of object to be removed and its hardness characteristics.

The suction force from the control means 90 may be on continuously to both remove collected material from within the passage means 40 and always assure a force in the direction of arrow 93 to pull it into and retain it against the jaws when they are in their open position. The thickness of each successive layer removed may be controlled by the spaced apart dimensional relationship of the cutting edges.

EMBODIMENT AS ILLUSTRATED IN FIGS. 6-9B

FIGS. 6-9B illustrate another embodiment of the present invention in which the instrumentation 30a has drive means 68a that may be operated by an electric motor 95a having power leads 96a connected thereto, which instrumentation is utilized when sufficient amounts of the object are to be removed and where the slower manual type of operation is not preferred. This embodiment of the invention contains jaws 36a and 38a which are of a different form than those previously illustrated and as will be illustrated with respect to FIGS. 10-12, but it should be pointed out that same are interchangeable with the jaws in the embodiment illustrated in FIGS. 1-5D and likewise the jaws of those illustrated figures may be used with the instrumentation 30a illustrated in FIG. 6.

It has been found desirable for certain removal procedures to provide a treatment fluid to the proximate location of the object and which treatment fluid is utilized for forming a suspension of the removed material which is then capable of being removed by a suction or other force from the removal means 31a leaving the worksite continually free of the removed material and likewise removing same from the removal means. Accordingly, the removal means 31a includes an inner assembly 42a and an elongate outer assembly 52a with a central longitudinal flow passage 55a with a central longitudinal flow passage 55a which essentially forms the passage means 40a. The outer assembly 52a includes a longitudinally extending jaw member 54a defining a jaw 38a or port at the distal end 32a thereof, which jaw member 54a is supported at its substantially opposite end by a support member 56a having a radial flange 98a for engagement with the support member of the outer assembly 52a. The support member 56a is removably secured at the front thereof to a threaded portion 99a of housing member 100a which has a radial flange 101a which abuts up against the front face 102a of the support member 56a and having a tubular wall portion 104a defining a pasagewaay 107a which has a downwardly extending tip 104a for sealingly engaging the outer diameter of the outer jaw member 54a after the lateral port holes 106a, which may be provided to extend through the wall of the outer jaw member 54a. At the opposite end of the housing member 100a we have a neck portion 108a extending therefrom with a plurality circumferentially spaced apart lateral ports 110a which communicate with the passageway 107a extending between the enclosed outer portion of the outer jaw member 54a and tubular wall portion 104a for providing a fluid flow channel to the front lateral ports 106a to obtain a flow in the initial direction of arrow 111a in the subsequent direction of arrow 112a, such that a fluid is supplied into the passage means 40a between the inner assembly 42a and outer assembly 52a.

The inner assembly 42a has an inner jaw member 45a which may be of a rod like shape with an enlarged jaw head 115a at one end thereof for defining the jaw 36a with a port extending therethrough between the parallel spaced apart faces 116a thereof, with cutting edges 87a extending along four edges as seen in FIGS. 7 and 8, and hereafter explained in greater detail. The inner jaw member 45a extends from a fastener 118a and may be integrally formed therewith such that the extension member 50a to which the fastener is secured is directly coupled to the power drive means 68a, having power cables 96a extending therefrom, as by threaded stud 120a. The casing of the drive means 68a has extending therefrom mounting means 65a in the form of a support arm 122a with a threaded portion adapted to receive the connecting member 124a which is connected to the tubular coupling member 58a which in turn is secured to the support member 56a.

To provide the requisite amount of treatment fluid from the control means a fluid conduit 125a is provided and may be coupled to a fluid supply hose not shown, and at one end thereof extends exteriorally of the removal means 31a from the connecting member 124a such that fluid in the direction of arrow 111a may flow therein and which forward portion of fluid conduit 125a extends within support member 56a in communicating relationship at its other end with a fluid supply port 126a within the support member 56a which opens into the spacing between the housing member 100a and the support member 56a so as to permit the flow into the inlet ports 110a. In like manner the removal means 31a for introducing the suction force in the direction of arrow 105a to remove the suspension that will be formed in the passage means 40a includes a suction conduit 128a extending exteriorally of and partially through the connecting member 124a at one end thereof and at its opposite end coupled to the support member 56a and in communicating relationship by the suction port 129a to the passage means 40a.

In this manner once the instrumentation 30a is positioned in place, in a similar manner as illustrated with respect to FIG. 1, the respective jaws 36a and 38a are then adapted to be moved angularly relative to each other as seen particularly in FIGS. 9, 9A and 9B, so that the removal of all or part of the object can be properly accomplished. The inner jaw member 36a is seen to include an enlarged head portion 115a having substantially parallel faces 116a with a transversely extending opening between the faces 116a forming the jaw or port therein and having spaced apart substantially parallel surfaces 85a terminating in cutting edges 87a on each side thereof so that it is possible to slice away or cut particles of the object as they are moved relative to each other. The end of the outer jaw 38a has a conical pointed seat 75a which is adapted to snugly receive the similarly contoured shape in the jaw 36a with the outer assembly 52a having a rounded front end 74a to assist its movement through the viscous, or other cellular material, until being positioned proximate to the object from which the material is to be removed.

The jaws 36a and 38a, may be formed to define sharp edges which act as cutting edges for severing or cutting of portions of the object extending therebetween, and as illustrated the outer jaw member 54a has a front end portion 73a having a contoured exterior surface 74a to facilitate its movement through the viscous material and an inner seat 75a, shown as a conical depression for receiving the complimentary shaped front end portion 77a of the inner jaw member 45a, with its conical exterior surface 78a which mates with the seat 75a for coaxial alignment therewith.

The outer jaw member 54a has therein the outer jaw defining opening or port 38a which is in communicating relationship to the passageway 55a and an oblong, elongated or oval shaped surface 80a having an outer edge 81a, and inner edge 82a preferably sharp to define a cutting edge, with the surface 80a inclined upwardly towards the cutting edge 82a from the outer edge 81a. The inner extremity of the outer member 82a or surface 80a should be above the axis of the outer jaw member 54a, and preferably a distance represented by the dimension X which is at least equal to the wall thickness of the outer jaw member 54a, so as to prevent rotation of tissue or other substances pulled by the penetrating point or cutting edges.

The inner jaw member 45a is similarly formed with the inner jaw defining an opening or port 56a which is in communicating relationship to the flow passage 55a and defines an oblong or elongated shaped surface 85a having parallel spaced apart inner edges 86a with spaced apart outer edges 87a preferably sharp to define a cutting edge with the surface 85a tapering upwardly from inner edge 86a to the outer edge 87a.

In order to form the suspension of removed material and fluid, which may be saline, the fluid may be supplied directly to the chamber means 40a as illustrated in FIGS. 6 and 7, or directly to the exterior of the removal means proximate to the jaws 36a and 38a, or directly to the passage means 40a and the removal site simultaneously. If it is desired that the fluid be supplied exteriorally of the removal means 31a then the lateral port holes 106a are adapted to extend through the tubular wall portion 104a as seen in FIG. 8, and if simultaneous supply of fluid is desired exteriorally and interiorally of the passage means 40a then the port holes 106a may be provided as in FIGS. 7 and 8.

OPERATION OF THE APPARATUS IN FIGS. 6–9B

In using the instrumentation 30a illustrated in FIGS. 6–9B it will be appreciated that first the removal means 31a is inserted such that the jaws 36a and 38a are positioned adjacent the object such that a portion thereof extends between the jaws, and by affecting relative movement of the jaws it is possible to sever any portion of the object extending therebetween as they are moved relative to each other. The removed material of the object is contained within the removal means 31a by entering the passage means 40a. By maintaining a differential pressure it is possible to maintain the object in fixed relationship to the jaws 36a and 38a such that as the cutting is obtained, the object, since it might be situated in a viscous material, is not forced away but is continuously engaged by at least one of the cutting edges 82a and 87a to progressively remove portions thereof.

The apparatus illustrated in FIGS. 6–9B is preferably used with a hardened object so that cutting may be facilitated by a static force being applied against the object towards the jaws to retain same in contact therewith. In this embodiment the differential pressure is obtained by using a suction force provided through the suction conduit 128a, suction port 129a which is in communicating relationship to the passage means 40a and in turn the jaws 36a and 38a, so that the object is continuously pulled between the jaws. Since the device illustrated, as seen in FIGS. 9–9B the inner jaw member 36a will continuously move through respective relative positions in a given cycle, and in the position shown in FIG. 9B has the cutting edge 87a in a parallel plane and adjacent the cutting edge 82a of the outer assembly 52a such that the material extending therebetween would be separated and removed as the angular rotation illustrated in FIGS. 9 and 9A occur. It is also possible by regulating the relative rate of movement between the jaws 36a and 38a per a given cycle, as well as the differential pressure by regulating the control means illustrated in FIG. 1, that the amount of material removed from the object and into the passage means 40a per given cycle may be properly controlled. The cycle, which is one complete revolution of the jaws relative to each other, is then repeated as many times as required until the amount of the object, which may be in its entirety, is removed from the body. In this manner by controlling the differential pressure it is possible to obtain a positionment of the object abuting the jaws 36a and 38a so as to progressively contact, cut and remove the material from the object as the jaws are moved relative to each other.

By properly controlling the dimentional relationship between the edge 82a of the outer jaw 38a to the cutting edge 87a of the inner jaw 36a it is possible to control the amount of removal of the material during the relative movement of the jaw members. One way of specifically doing same is that by coaxially supporting the jaws 36a and 38a to provide a selected configuration of a given internal cross-sectional area for one of the cutting edges 82a and providing the other cutting edge 87a with a similar configuration but of an enlarged cross-sectional area such that the thickness of the layer of material removed is equal to the difference between the respective cross-sectional areas if both are circular or the lateral spacing between the cutting edges.

The control means is adapted to continuously supply a fluid to the removal means 31a to assist in the removal operation of the object. The fluid which may be in the form of a liquid may be provided for various reasons, one of which is to replenish the removed material from the object as well as any vitreous material lost in the procedure in order to maintain the internal pressure of the eye to prevent collapse of the retina and related portions. The eye has an internal pressure and unless the removed material is replenished there is a tendency for the wall of the eye to collapse which could severely complicate the surgical procedure. Another important reason for supplying the treatment fluid it to form a suspension with the removed particles so that they are easily removed by suction from the removal means 31a.

Particularly noting FIG. 8, I illustrate an aspect of the invention in which if desired the liquid may be supplied exteriorally of the removal means 31a and proximate to the object by having the lateral ports 106a extending through the housing member wall 104a such that the treatment liquid and the suction is applied proximate to the object at spaced apart locations between which at least a section of the removal means 31a is interposed so that the suction induces the treatment liquid to mix with the removed material for ensuring the continuous mixing of the removal of the material. In addition the motion of the fluid will carry the material between the jaws.

In operation the operator after positioning the instrumentation 30a in position will adjust the fluid control knob on the control means and the fluid from a supply will enter the fluid conduit 125a in the direction of arrow 111a and then by means of fluid supply port 126a and lateral port holes 106a will reach the interior of passage means 40a, the exterior of the removal means 31a adjacent the jaws 36a and 38a, or as explained above both the interior and exterior. Since the jaws 36a and 38a in FIGS. 6–9B are essentially always open the suction force is simultaneously maintained such that a flow pattern is established into the passage means 40a in the direction of arrow 111a and thereafter cut in the direction of arrow 112a through the suction conduit 126a. Simultaneously with the fluid being supplied and suction force applied the drive means 68a is operational effecting rotation of the inner jaw 36a with the resulting cutting of the object. The motor 95a of drive means 68a may be of a variable speed type which is adjusted by the user depending on the quantity and type of object being removed. After removing the desired amount the drive means 95a is stopped with the fluid supply and suction being discontinued by adjusting the control means. The removal means 31a is then retracted from within the body and the opening closed.

OTHER JAW CONTSTRUCTIONS

FIGS. 10, 11 and 12 illustrate other alternate jaw construction forms of jaw members that may be used for removal of the material as desired. FIGS. 10 and 11, illustrate an inner jaw member 36b and outer jaw member 38b with the latter having its outer assembly 52b of similar construction to that illustrated in FIGS. 6–9B with the outer jaw member 54b having a front end portion 73b with an inner seat 75b, shown as a conical depression for receiving the complimentary shaped front end portion 77b of the inner jaw member 45b with its conical frontal exterior surfaces 78b which mates with seat 75b for coaxial alignment therewith. The inner jaw 36b has its inner jaw member 45b forced having an outwardly radially extending helical groove 130b running essentially the length thereof and having a conical tip 78b at one end thereof such that the cutting edge surface 87b thereof which forms the jaw 36b is seated within the outer assembly 52b which has the jaw 38b defining an opening so as to communicate with the passage means 40b, and as they are moved relative to each other the helical groove 130b continues to remove the object which moves along the passage means 40b permitting the continuous removal of both the material and the liquid. The liquid is supplied by the flow passage 107b which extends between the housing member 100b and outer assembly 52b with the lateral ports 106b in communicating relationship with the passage means 40b as indicated by the arrow 112b such that the flow of liquid and removed material mixes therein and due to the angular rotation of the inner assembly 42b the removal thereafter occurs. The mechanical structure of the drive means for the tools illustrated in FIGS. 10 and 11 may be of the design illustrated in FIG. 2 and or FIG. 6.

FIG. 12, illustrates another form of the jaws 36c and 38c in which the inner assembly 42c includes a jaw member 45c having a longitudinally extending shaft 132c with a chisel point 133c at one end thereof and having circumferentially wound about the exterior surface of the shaft 132c the helical defining groove 130c such that it acts as a pumping means for removal of the material. The outer jaw 38c defining a lateral opening therein with the outer assembly 52c having front end portion 73c with at least a flat interior surface or seat 75c such that the chisel edge portion 87c abuts it and as the angular movement is obtained removal of the object occurs. In like manner fluid may be pumped in through the passage means 40c and by the mixture forming and the pumping action obtained by the helical grooves, the material is continuously removed from the removal means 31c. This helical mechanism may provide a controlled method of pumping materials with low viscosity (natural or synthetic vitreous) into the body. To prevent the collapse of the eye this mechanism may be used in that it can supply and remove vitreous at a controlled rate.

CATARACT REMOVAL PROCEDURE

Before discussing in detail the use of the present invention for lens removal it might be best to first review in greater detail certain known facts to date. A cataract is a lens opacity and to better understand its implications we have to learn more about the lens.

Anatomy of the Lens: The lens is a biconver almost completely transparent structure, about 5mm thick and 9mm in diameter. It is suspended behind the iris by the zonular fibers, which connect it with the ciliary body. The lens is incapsulated in the lens capsule, which is a thin transparent membrane, of which the front part is called the anterior capsule, and the back part is called the posterior capsule. Behind the posterior capsule is the vitreous membrane. The posterior capsule and the vitreous membrane are not easily separable in a young person. The lens is composed of a central region or nucleus and the peripheral portions is called the cotex, the nucleus is harder than the cortex.

Function of the Lens: The function of the lens is to focus light rays upon the retina. In order to focus light from a distant object, the ciliary muscle relaxes, tightening the zonular fibers and reducing the thickness of the lens to its minimal dimension, in this position parallel rays are focused on the retina. In order to focus light rays from a near object the ciliary muscle releases the tension on the zonules fibers, the lens shapes in a more spherical body increasing its refractive power so that the focusing on the retina is again obtained.

Composition of the Lens: The lens consists of about 65% water and about 35% protein (with some trace of minerals).

Cataract: A cataract is a lens opacity. Cataracts vary markedly in degree of opacity, size and location. Cataracts may be due to a variety of causes but are usually associated with ageing. Most cataracts are not visible to the casual observer until they become dense enough (mature) to cause blindness.

We have several types of cataracts:

1. A senile cataract is the most common type associated with ageing. After surgery the visual (acuity) improves in over 90% of the cases, the remainder either have pre-existing retinal damage or develop post-surgical complications.

2. Congenital Cataract: They occasionally occur as a consequence of maternal rubella due the first three months of pregnancy. These cataracts may cause significant loss of vision, in such event lens extraction by aspiration is done on one eye at the age of six months. Surgery on the other eye is performed after the age of two (retina detachment may occur after several months or years).

3. Traumatic Cataract: Most commonly due to a foreign body striking the lens after passing through the outer structure of the eye, such a cataract may also be caused by over-exposure to heat, x-ray, radioactive material and ultraviolet exposure.

4. Cataract may also occur as a secondary effect of intraocular or systemic diseases, as well as a result of some drugs.

Cataract Surgery: In a cataract operation the lens is removed from the eye. At the present time there are two principal types of lens extraction, they are:

1. Intracapsular when the lens is removed together with the capsule, this is a standardized procedure. When the posterior capsule is not attached to the vitreous membrane.

2. Extracapsular extraction is used in congenital and some traumatic cataracts. As we know the posterior capsule may be attached to the membrane and cannot be extracted without rupturing the vitreous membrane, with serious consequences (vitreous loss, vitreous hemorrhage, retina detachment, etc). For this operation, the anterior capsule is first ruptured and removed then the cortex and nucleus, leaving the posterior capsule behind.

At the present time a solution of chymotrypain is injected under the iris. This substance has a lytic (loosening) action on the zonules making easier the removal of the lens. To perform the actual operation of extracting the cataractous lens a conjunctival incision is made 3mm from the limbus on an arc about 20mm long, extending from 9 to 3 o'clock, at 12 o'clock a peripheral or full iredectomy is then performed and the lens and capsule is grasped and gently removed from the eye. The conjunctival flap is reapproximated with the sutures. The anterior chamber is then reformed by injection of soline. If the procedure is complicated by vitreous loss, the changes of post operative retinal detachment, glaucoma, and uveitis are increased.

Post operative care consists in having the eye bandaged for about two weeks, the patient has to move slowly and avoid any strain for about four weeks. The material removed from the eye at the present time by the conventional intracapsular cataract operation can now be extracted through a 1 to 2mm incision.

CATARACT PROCEDURE OF PRESENT INVENTION

By using the new and novel method of the present invention, in accordance with one aspect thereof an intracapsular procedure can be performed, the incision can be made at any convenient place, no iredectomy is necessary for this operation. The instrument of the present invention is not inserted into the eye through the small incision with the opening at its front, gently pressing against the capsule. By rotating the internal cutter jaws, material from the capsule and later from the lens is being chopped away from the mass to be removed, by carefully orienting the front of the tip it is possible to reach any remaining portion of the capsule or lens. When only suction is needed the internal cutter jaw is stopped in such a position not to block the front opening. It is important to emphasize that only one piece (becoming smaller and smaller) of capsule and one piece of lens is left in the eye during the operation. The operation continues until the whole lens is extracted. Extraction of the posterior capsule is optional.

Irrigation of the anterior parts of the eye is necessary to maintain the pressure in the eye above the atmospheric pressure to prevent its collapsing and to facilitate movement of the chopped material in liquid suspension from the eye. After the lens and the desired amount of capsule is removed, the instrument is extracted and the incision closed with a single suture as with an ultrasonic or other weld. Post operative care by use of the present invention is greatly reduced due to the single stitch in place of many and the relatively short incision (about 1/10 to 1/15 of the regular one). The possibility of infection and retina detachment is also reduced due to the small incision and maintained pressure in the eye at all times. The instrument used to perform such a transfusion of relatively dense, high viscosity liquid, may be as shown in FIG. 12.

In accordance with another aspect of the invention an extracapsular can be performed in which a different procedure is used so that the capsule should remain in the eye. For such a case a 20mm incision on the outer wall of the eye is needed to be able to reach the anterior capsule with the instrument. A 1-2mm incision is now made on the anterior capsule through which the instrument is now inserted. The material to be removed is now the lens alone which is being chopped by the instrument, parts of the lens are now removed as previously described until the entire lens is extracted. By keeping the liquid pressure in the capsule the lens will practically float in it and will be kept adjacent to the cutting instrument by the force of the moving liquid as well as by the differential pressure which generates this flow. As described previously the remainder of the lens in the capsule is always confined in one piece which is getting smaller and smaller during the operation until the last piece is being removed. After the operation the instrument is extracted, or while in position the capsule may be refilled with a specific natural or artificial liquid to replace the lens, the instrument shown on FIG. 12, can be used to inject or drive into the capsule liquid of high viscosity, the capsule now has to be closed by a suture or by an ultrasonic or other weld. The outer incision is also closed by sutures or weld, the anterior chamber reformed and if everything went as expected no glasses or contact lenses will be needed.

Figure 15:
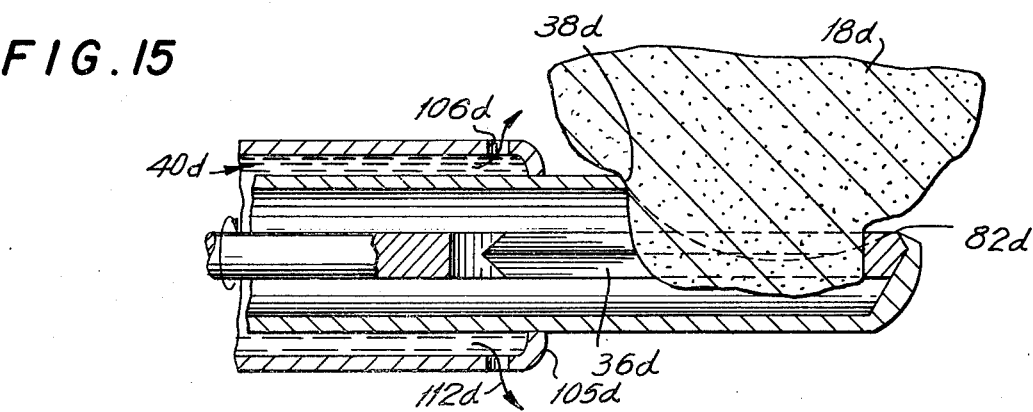
FIG. 15, is a further enlarged and fragmentary side view in section illustrating the removal process of the lens from the eye.
Figure 16:
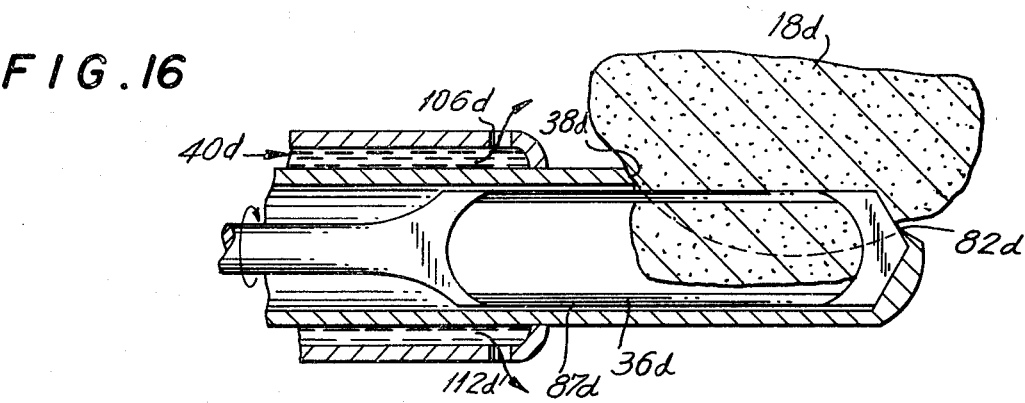
FIG. 16, is a view similar to FIG. 15, showing the jaws in a different position relative to each other.
Figure 17:
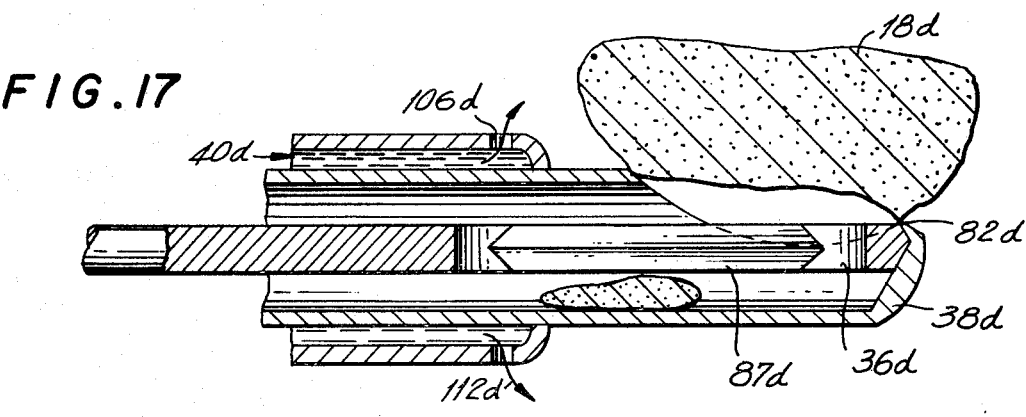
FIG. 17, is a view similar to FIG. 15, showing the jaws in a different position relative to each other.

FIGS. 13-17, illustrate the use of the apparatus generally seen in FIGS. 6-9B for cataract surgery, within the eye 10d, and in which we have the removal of an object of high viscosity or hardened material requiring a continuous cutting and removal as described. The use of the invention takes into consideration the desirability of maintaining the pressure constantly above the atmosphere within the eye chamber or capsule such that it does not collapse as the lens is gradually removed during the operation. It is possible to maintain the pressure by retaining the volume of material within the eye chamber or capsule constant such that we have an equal volume of liquid therein. The incoming liquid has to replace the liquid being lost through the incision and the material being removed in subsequent removal steps. The operation includes forming an incision, if desired using the supporting means illustrated in FIG. 1 in conjunction with a double mattress suture which is used to tighten the eye wall around the tip to maintain the pressure in the eye and prevent appreciable amounts of liquid losses through the incision with consequent increase in flow into and through the eye in which case the streaming of the liquid may cause damage to the single layer of cells of the inner surface of the cornea forming the endothelium. By this surgical procedure it is possible to maintain the lens material to be removed by suction and force of moving liquid in contact with the removal means $31d$ between the successive cut. Once the instrumentation $30d$ is embedded within the lens material $18d$, and as seen in FIGS. 15, 16 and 17 by utilization of the suction force we have a portion of the lens $18d$ extending between the jaws $36d$ and $38d$ and within the opening of the inner jaw $36d$. Once the object $18d$ is positioned as seen in FIG. 15 and the angular movement between the respective jaw members $36d$ and $38d$ is obtained we have a continued slicing of particles and removal thereof. As indicated above a fluid is used and accordingly we may have the exterior port holes $106d$ as indicated by arrow $112d$ providing a liquid medium within the eye chamber or capsule such that it assists in the formation of a liquid suspension which is easily removable by suction means transmitted to the removal means $31d$ as hereinabove described.

For the extracapsular procedure, once the opening is formed in the anterior capsule and the instrument is inserted, a differential pressure is applied as by combined suction and pressure of incoming liquid, the instrumentation $30d$ is moved forwardly into the lens that the distal end $32d$ thereof and particularly the jaws $36d$ and $38d$ come in contact with the material and when the static pressure in the capsule is such to force liquid in between the lens and the capsule this facilitates limited motion of the lens in the capsule even at the beginning of the operation such that the lens almost somewhat floats and is separated from the capsule. The vacuum in the passage means $40d$ causes the lens material $18d$ to remain adjacent to the cutting edges $82d$ and 87d to shear the lens mass when exposing it to the rotating cutting edges such that consequentially the edges cut a slice of the mass of the lens 18d and continues to remove same into the passage means 40d. As this operation continues it can easily be appreciated that the entire mass can be removed.

An important aspect of the present invention is the fact that it is possible to remove the lens alone without actually engaging or damaging, except for a small minimal opening formed of perhaps two milimeters, the anterior capsule. By being able to remove the inner core without physically damaging the exterior capsule it becomes possible to replace the lens material with a liquid material that would permit the same transparency such that it would not be necessary to remove the actual capsule itself. This is most important in that if the remaining portions are kept intact and the zonules has remained in functioning condition then by replacing the lens material with another type of material a person can continue to use same as he had before without having to resort to contact lenses and this is substantially important. Accordingly, supply means 135d, which may be represented by FIG. 12, may be inserted into the anterior capsule and by conventional control means associated therewith (not shown) replenish the removed lens at a speed equal to the removal rate to thereby obtain a complete transfusion of the lens with a liquid.

CONCLUSION

The above discussion clearly indicates that the present invention may be used for the removal of a variety of objects from humans or animals in vivo as desired, and particularly is related to the areas associated with the eye in view of the unique characteristics and problems associated such as that the pressure should be accounted for and retained. This differential of pressure between the exterior and interior of the eye also lends itself to assist in the actual process as well as create the unique problems associated therewith. Accordingly, the instrumentation is adaptable to be used herein by these skilled in the field for removal of select objects as desired and at rates that are appropriate for the portion involved. This permits the insertion of the instrumentation, its positioning and remaining in a given region until removed from the opening, which opening is then closed in a conventional manner.

In particular with respect to cataract removal we have the unique ability if desired to permit the lens capsule to remain in tact while removing the lens therefrom. It should be pointed out that this ability substantially lessens the dangers associated therewith and particularly increases the comforts to the individual who is operated on in this procedure.

Although illustrative embodiments of the invention have been described in detail herein with reference to the accompanying drawing, it is to be understood that the invention is not limited to those precise embodiments, and that various changes and modifications may be effected therein without departing from the scope or spirit of the invention, except as defined in the appended claims.

I claim:

1. A method of severing and removing material from an object from within the body of a human being or other animal in vivo with removal means including passage means and a pair of material severing jaws which are movable relative to each other in communication with the passage means comprising the steps of:

A. forming an opening through the body to gain access to said object,
   B. inserting in said body, said removal means through said opening,
   C. positioning said removal means proximate to said object for engagement with said jaws,
   D. maintaining a suction force in said passage means to retain at least a portion of said object substantially adjacent to said jaws,
   E. effecting relative movement of said jaws to an open position permitting material to enter said passage means and then further effecting relative movement of said jaws so as to sever any material of the object extending therebetween, said removed material of said object being contained within said removal means, and
   F. removing the material severed from the object from within said removal means by the suction force maintained in the passage of said removal means.

2. A method as in claim 1 including the step of maintaining said suction force to a degree sufficient to obtain a positionment of said object abutting said jaws so as to progressively contact, sever and remove material from said object and transfer the severed material into said passage means as the jaws are moved relative to each other.

3. A method as in claim 1, and further including the step of controlling the amount of material removed during the relative movement between said jaws.

4. A method as defined in claim 3 wherein said step of controlling the amount of removal includes the step of regulating the relative rate of movement between said jaws and said suction force.

5. A method as defined in claim 3, and further including the step of repeating the movement of the jaws relative to each other as required until the entire object is removed from said body.

6. A method as in claim 1 further comprising the step of forming the jaws of the removal means to substantially block the entry of material into said passage means when the jaws are in the closed position, and maintaining said jaws are in a closed position when said removal means is inserted in said body to prevent material from entering the passage means, and thereafter first effecting relative movement between said jaws from their closed to open position to facilitate positioning of said material in said passage means.

7. A method as in claim 1, and further including the steps of:
   a. supplying a treatment fluid proximate to said object so that the material removed by said jaws forms a mixture with said fluid resulting in a suspension thereof, and
   b. simultaneously applying said suction force to said suspension to remove said suspension into said passage means through said jaws.

8. A method as in claim 7, including the steps of supplying said treatment fluid proximate to said object and applying the suction proximate to said object at spaced apart locations between which at least a section of said removal means is interposed so that the suction induces the treatment liquid to mix with the removed material for ensuring the continuous mixing and the removal of said material.

9. A method as in claim 8, step of supplying treatment fluid interiorly of said removal means.

10. A method as in claim 19, including the step of supplying said treatment fluid exteriorly of said removal means.

11. A method as in claim 1, further including the step of maintaining said portion of the body during the removal of said object at substantially its normal internal pressure, to prevent collapse of said portion.

12. A method as in claim 11, including the steps of maintaining said internal pressure by simultaneously supplying a fluid within said body portion in relationship to the rate of removal of the object therefrom and any losses of liquid through any incision.

13. A method of severing and removing material from an object from the eye of a human being or other animal in vivo, with
removal means including passage means and a pair of material severing jaws which are movable relative to each other communicating with the passage means comprising the steps of
providing an opening in the eye to gain access to said object,
inserting in said eye through said opening said removal means in its closed position,
positioning said removal means proximate to said object for engagement with said jaws,
placing said jaws in an open position,
maintaining a suction force in said passage means to maintain said object in engagement with said jaws while said jaws are in their open position,
effecting relative movement of said jaws so as to sever any material of the object extending therebetween as they are moved relative to each other, from their open to a more closed position, said removed material of said object being contained within said passage means,
and removing the material from said passage means by said suction force.

14. A method as in claim 13, including the step of maintaining
said suction force at a pressure sufficient to obtain a flow of said object within said passage means when said jaws are in their open position.

15. A method of removing a layer of material from an object within the eye of a human being or other animal in vivo, comprising the steps of:
providing removal means of the type including passage means and a pair of jaws defining cutting edges communicating with the passage means adjacent one end thereof, with said jaws adapted to be rotating relative to each other such that there is a substantial component of angular motion therebetween, comprising the steps of:
providing an opening in the eye in gain access to said object,
inserting in said eye through said opening said removal means,
positioning said removal means proximate to said object for engagement with said jaws,
maintaining a suction force in said passage means to retain said object in substantially fixed position relative to said jaws, and
effecting relative rotational movement of said jaws so as to progressively contact, cut and thereby remove a layer of material from said object and into said passage means,
and transferring the removed material from said passage means using the suction force.

16. A method as in claim 13, and further including the steps of:
a. supplying a treatment fluid proximate to said object so that the material removed by said jaws during each cycle forms a mixture with said fluid resulting in a suspension thereof, and
b. simultaneously applying a suction force to said suspension to remove said suspension into said passage means through said jaws.

17. A method of extracapsular eye surgery in vivo, comprising the steps of:
A. progressively removing material from the lens of the eye from within its capsule and withdrawing the material from said capsule, and
B. replacing the removed lens material of the eye with a fluid material in said capsule, whereby the eye may thereafter function with said fluid contained therein.

18. A method as in claim 17, and further including the step of separating the lens from said capsule by introducing a fluid into said capsule to facilitate progressively removing the lens.

19. A method of eye surgery in a human being or other animal in vivo, comprising the steps of:
A. providing an opening through the eye to gain access to the lens,
B. progressively removing by mechanical severing action of two cutting members moving relative to each other material from the lens of the eye from within its capsule and withdrawing said material from said capsule, and
C. simultaneously internally supporting the capsule during removal of said lens material to prevent collapse of said capsule.

20. A method as in claim 19, wherein said step of simultaneously supporting the capsule during removal of said lens material therefrom to prevent collapse thereof comprises supplying, a fluid in replacement of the lens material removed.

21. A method of eye surgery in a human being or other animal in vivo, comprising the steps of:
A. providing an opening through the eye to gain access to the lens,
B. progressively removing the lens of the eye from within its capsule, by:
1. inserting in said capsule in engagement with said lens a removal means including passage means and a pair of jaws having cutting means thereon in communication with said passage means adjacent one end thereof, said jaws adapted to be moved relative to each other,
2. maintaining a suction in said passage means to retain said lens in substantially fixed position relative to said jaws,
3. effecting relative movement of said jaws so as to sever the material of the lens extending therebetween as they are moved relative to each other, said removed lens material being received within said passage means, and
4. withdrawing the removed lens material from the capsule, and
C. simultaneously internally supporting the capsule during removal of said lens to prevent collapse thereof by supplying a fluid in replacement of the lens material removed.

22. A method of removing cataracts, comprising; positioning within the body of an organic eye and interiorly of an organic crystalline lens capsule containing a cataract the end of a hollow elongate member having an opening at the end thereof; inserting a masticating tool through said hollow member; masticating the interior contents of said capsule; withdrawing the masticated capsular contents through said hollow member; and injecting a transparent fluid filler material into said lens capsule following withdrawal of the masticated contents thereof.

\* \* \* \* \*